US 6,706,689 B2

(12) United States Patent
Coolidge et al.

(10) Patent No.: US 6,706,689 B2
(45) Date of Patent: Mar. 16, 2004

(54) TREATMENT OF ACUTE CORONARY SYNDROME WITH GLP-1

(75) Inventors: Thomas R. Coolidge, Falls Village, CT (US); Mario Ehlers, Lincoln, NE (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 23 days.

(21) Appl. No.: 09/859,804

(22) Filed: May 18, 2001

(65) Prior Publication Data

US 2002/0107206 A1 Aug. 8, 2002

Related U.S. Application Data

(60) Provisional application No. 60/205,239, filed on May 19, 2000.

(51) Int. Cl.$^7$ ............................................... A61K 38/22
(52) U.S. Cl. ............................................... 514/12; 514/2
(58) Field of Search ....................................... 514/12, 2

(56) References Cited

U.S. PATENT DOCUMENTS

| 6,277,819 B1 | * | 8/2001 | Efendic ..................... 514/12 |
| 6,348,447 B1 | * | 2/2002 | Hellstrom et al. ............ 514/12 |
| 6,358,924 B1 | * | 3/2002 | Hoffmann .................... 514/12 |

FOREIGN PATENT DOCUMENTS

| WO | WO 98/08531 | 3/1998 |
| WO | WO 00/66138 | 11/2000 |
| WO | WO 00/66142 | 11/2000 |

OTHER PUBLICATIONS

Frost et al., "Effect of Large Bowel Fermentation on Insulin, Glucose, Free Fatty Acids, and Glucagon–Like Peptide 1 (7–36) Amide in Patients with Coronary Heart Disease," Nutrition, vol. 15, No. 3, Elsevier Science Inc., pp. 183–188.

Nikolaidis et al., "GLP–1 Improves Myocardial Performance in Consclous Dogs with Pacing Induced Heart Failure," Journal of the American College of Cardiology, vol. 37, No. 2 Supplement A, 50$^{th}$ Annual Scientific Session of the American College of Cardiology, Orlando, Florida, USA, Mar. 18, 2001, 1 sheet.

* cited by examiner

*Primary Examiner*—Jon P. Weber
(74) *Attorney, Agent, or Firm*—Molly A. Holman; Mi K. Kim; Arnold & Porter

(57) ABSTRACT

The invention relates to methods for treating a patient suffering from acute coronary syndrome, but who is not suffering from a Q-wave myocardial infarction, comprising administration of a therapeutically effective amount of a GLP-1 molecule. The GLP-1 can be self-administered, and can be administered in one or more doses, as needed, on an intermittent or continuous basis, to optimize metabolism in cardiac tissue and to prevent cardiac damage associated with ischemia.

41 Claims, No Drawings

SEQUENCE LISTING

```
<160> NUMBER OF SEQ ID NOS: 13

<210> SEQ ID NO 1
<211> LENGTH: 37
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 1

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 2

His Asp Glu Phe Glu Arg His Ala Glu Gly Thr Phe Thr Ser Asp Val
```

```
                1               5              10              15
Ser Ser Tyr Leu Glu Gly Gln Ala Ala Lys Glu Phe Ile Ala Trp Leu
               20              25              30

Val Lys Gly Arg
       35

<210> SEQ ID NO 3
<211> LENGTH: 31
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 3

His Ala Glu Gly Thr Phe Thr Ser Asp Val Ser Ser Tyr Leu Glu Gly
 1               5              10              15

Gln Ala Ala Lys Glu Phe Ile Ala Trp Leu Val Lys Gly Arg Gly
               20              25              30

<210> SEQ ID NO 4
<211> LENGTH: 30
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 4

His Ala Glu Gly Thr Phe Thr Ser Asp Val Ser Ser Tyr Leu Glu Gly
 1               5              10              15

Gln Ala Ala Lys Glu Phe Ile Ala Trp Leu Val Lys Gly Arg
               20              25              30

<210> SEQ ID NO 5
<211> LENGTH: 29
<212> TYPE: PRT
<213> ORGANISM: Unknown Organism
<220> FEATURE:
<223> OTHER INFORMATION: Description of Unknown Organism: Truncated form
      of GLP-1

<400> SEQUENCE: 5

Glu Gly Thr Phe Thr Ser Asp Val Ser Ser Tyr Leu Glu Gly Gln Ala
 1               5              10              15

Ala Lys Glu Phe Ile Ala Trp Leu Val Lys Gly Arg Gly
               20              25

<210> SEQ ID NO 6
<211> LENGTH: 28
<212> TYPE: PRT
<213> ORGANISM: Unknown Organism
<220> FEATURE:
<223> OTHER INFORMATION: Description of Unknown Organism: Truncated form
      of GLP-1

<400> SEQUENCE: 6

Glu Gly Thr Phe Thr Ser Asp Val Ser Ser Tyr Leu Glu Gly Gln Ala
 1               5              10              15

Ala Lys Glu Phe Ile Ala Trp Leu Val Lys Gly Arg
               20              25

<210> SEQ ID NO 7
<211> LENGTH: 39
```

```
<212> TYPE: PRT
<213> ORGANISM: Unknown Organism
<220> FEATURE:
<223> OTHER INFORMATION: Description of Unknown Organism: Exendrin 3

<400> SEQUENCE: 7

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 8
<211> LENGTH: 31
<212> TYPE: PRT
<213> ORGANISM: Unknown Organism
<220> FEATURE:
<223> OTHER INFORMATION: Description of Unknown Organism: Exendrin 4
      (9-39(NH2)

<400> SEQUENCE: 8

Asp Leu Ser Lys Gln Met Glu Glu Glu Ala Val Arg Leu Phe Ile Glu
 1               5                  10                  15

Trp Leu Lys Asn Gly Gly Pro Ser Ser Gly Ala Pro Pro Pro Ser
                20                  25                  30

<210> SEQ ID NO 9
<211> LENGTH: 39
<212> TYPE: PRT
<213> ORGANISM: Unknown Organism
<220> FEATURE:
<223> OTHER INFORMATION: Description of Unknown Organism: Exendrin 4

<400> SEQUENCE: 9

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 10
<211> LENGTH: 38
<212> TYPE: PRT
<213> ORGANISM: Unknown Organism
<220> FEATURE:
<223> OTHER INFORMATION: Description of Unknown Organism: Helospectin I

<400> SEQUENCE: 10

His Ser Asp Ala Thr Phe Thr Ala Glu Tyr Ser Lys Leu Leu Ala Lys
 1               5                  10                  15

Leu Ala Leu Gln Lys Tyr Leu Glu Ser Ile Leu Gly Ser Ser Thr Ser
                20                  25                  30

Pro Arg Pro Pro Ser Ser
            35

<210> SEQ ID NO 11
<211> LENGTH: 37
<212> TYPE: PRT
<213> ORGANISM: Unknown Organism
<220> FEATURE:
<223> OTHER INFORMATION: Description of Unknown Organism: Helospectin II
```

```
-continued

<400> SEQUENCE: 11

His Ser Asp Ala Thr Phe Thr Ala Glu Tyr Ser Lys Leu Leu Ala Lys
 1               5                  10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 12
<211> LENGTH: 35
<212> TYPE: PRT
<213> ORGANISM: Unknown Organism
<220> FEATURE:
<223> OTHER INFORMATION: Description of Unknown Organism: Helodermin

<400> SEQUENCE: 12

His Ser Asp Ala Ile Phe Thr Glu Glu Tyr Ser Lys Leu Leu Ala Lys
 1               5                  10                  15

Leu Ala Leu Gln Lys Tyr Leu Ala Ser Ile Leu Gly Ser Arg Thr Ser
            20                  25                  30

Pro Pro Pro
        35

<210> SEQ ID NO 13
<211> LENGTH: 35
<212> TYPE: PRT
<213> ORGANISM: Unknown Organism
<220> FEATURE:
<223> OTHER INFORMATION: Description of Unknown Organism: Q8, Q9
      heliodermin

<400> SEQUENCE: 13

His Ser Asp Ala Ile Phe Thr Gln Gln Tyr Ser Lys Leu Leu Ala Lys
 1               5                  10                  15

Leu Ala Leu Gln Lys Tyr Leu Ala Ser Ile Leu Gly Ser Arg Thr Ser
            20                  25                  30

Pro Pro Pro
        35
```

TREATMENT OF ACUTE CORONARY SYNDROME WITH GLP-1

RELATED APPLICATION

This application claims priority to U.S. provisional application No. 60/205,239, filed May 19, 2000, which is incorporated in its entirety herein by reference.

BACKGROUND OF THE INVENTION

Heart disease is a major health problem throughout the world. Myocardial infarctions are a significant source of mortality among those individuals with heart disease.

Acute coronary syndrome ("ACS") denotes patients who have or are at high risk of developing an acute myocardial infarction (MI). This complex includes unstable angina (UA), non-Q-wave cardiac necrosis (NQCN) and Q-wave MI (QMI). Thompson et al., *M.J.A.* 171; 153 (1999). Typically, ACS is diagnosed when a patient has acute (i.e., sudden onset) chest pain of a cardiac origin that is either new or clearly different from pre-existing, chronic, stable angina; that is, ACS chest pain is more severe, more frequent, occurs at rest, or is longer than 15 minutes in duration. After ACS has been diagnosed, the patient is stratified into UA, NQCN, and QMI, using criteria that are described elsewhere in this application. UA, NQCN, and QMI are believed to represent different stages of plaque rupture and thrombosis. Zaacks et al., *J. Am. College Cardiol.* 33; 107 (1999). With UA, there typically is no myocardial necrosis. Id. UA, NQCN, and QMI all are characterized by varying degrees of ischemia. Id. Additionally, Q-wave MI generally is understood to result from total occlusion of a coronary artery, whereas UA is caused by a subtotal occlusion. Thompson et al. *M.J.A.* 171; 153 (1999).

During normal, aerobic metabolism, cardiac tissue uses free fatty acids (FFA) to generate energy. During ischemia induced by UA, NQCN, or Q-wave MI, the heart switches to anaerobic metabolism, using glucose as its primary energy source.

Many other detrimental metabolic changes occur during ischemia in cardiac tissue, including accumulation of excess unoxidized FFA products, inhibition of $Ca^{2+}$ and $Na^+/K_+$ pumps, and increased levels of cAMP. Additionally, there is decreased secretion of insulin by pancreatic β-cells and excess secretion of glucagon by pancreatic α-cells.

Excess glucagon can lead to myocardial tissue damage; glucagon is also an insulin antagonist and mediates lipolysis in adipose tissue, with release of FFAs. Excess FFAs can lead to free radical formation and consequent tissue damage. Glucagon is one of the so-called counter-regulatory hormones, a group that includes cortisol, growth hormone, and catechlolamines, which are released during "stress" conditions, such as ACS, UA, NQCN, fasting, starvation, infection, disease, internal injury, and trauma. The role of such hormones is to counter-regulate the effects of insulin, thereby raising blood glucose and fatty acid levels and producing a generally insulin-antagonistic state. Glucose is a mediator of stress responses and a component of systemic inflammatory reactions.

A variety of therapeutic agents is known for treating Q-wave MI. These include thrombolytic therapy and angiotensin-converting enzyme (ACE) inhibitors. Thompson et al., *M.J.A.* 171; 153 (1999). PCT Application WO 98/08531 relates to treatment with GLP-1 of a patient suffering from Q-wave MI who is also incapable of auto-regulation of blood glucose.

Agents known for treatment of a subtotal coronary occlusion, which results in UA, include heparin, low-molecular-weight heparin, and nitroglycerine. Thompson et al., *M.J.A.* 171; 153 (1999). β-blockers can be used to combat myocardial ischemia and left ventricular dysfunction that result from acute MI and UA. Id. Prior to the formation of a fibrin thrombus, which leads to partial or total coronary artery occlusion, it is known that that there is plaque erosion or fissure, followed by platelet aggregation. This aggregation can be treated with aspirin, glycoprotein IIb/IIIa antagonists or clopidogrel. Thompson et al., *M.J.A.* 171; 153 (1999).

Most therapies for the treatment of UA work by (1) stabilizing or reducing the occlusion, such as the anti-thrombin agents heparin and low-molecular-weight heparin, and the anti-platelet agents aspirin, glycoprotein IIb/IIIa antagonists, or clopidogrel, (2) reducing preload, such as nitroglycerine, (3) reducing afterload, such as ACE inhibitors, or (4) reducing myocardial oxygen demand, such as β-blockers. These therapies do not treat directly the disturbed energy metabolism that results from ischemia and that induces tissue damage. Also, dosages of drugs such as heparin must be controlled carefully to avoid toxic effects of overdose.

As a result, there is a need for therapeutic treatments that can be used preferably beginning at the earliest stages of ACS, and during UA or NQCN, and that will prevent and/or reduce the damage resulting from ACS, including any subsequent Q-wave MI.

SUMMARY OF THE INVENTION

Objects of the present invention include the following:
(1) A method of treating a patient suffering from acute coronary syndrome, comprising administering to the patient a therapeutically effective amount of a GLP-1 molecule, wherein the patient is not suffering from a Q-wave MI. The above method, wherein the patient is suffering from unstable angina. The above method, wherein the patient is suffering from non-Q-wave cardiac necrosis. The above method, wherein the patient has a blood troponin I level of no more than 0.4 ng/ml. The above method, wherein the patient has a blood troponin T level of no more than 0.1 ng/ml. The above method, wherein the patient does not have elevated blood creatine kinase. The above method, wherein the patient does not have ST-segment elevation. The above method, wherein the patient does not exhibit a pathological Q-wave. The above method, wherein the patient exhibits one or more of the following symptoms: chest pain greater than 15 minutes in duration, chest pain at rest, or chest pain following minimal exertion that is poorly responsive to sublingual nitrates. The above method, wherein the patient has stable angina. The above method, wherein the patient administers the GLP-1 to himself. The above method, wherein the GLP-1 is administered in the form of a GLP-1-stick. The above method, wherein the GLP-1 is administered in a single dose. The above method, wherein the GLP-1 is administered in more than one dose. The above method, wherein the GLP-1 is administered continuously. The above method, wherein glucose, or a potassium salt, or a combination thereof, is co-administered with the GLP-1.
(2) A method for treatment of a patient, comprising administering to the individual a therapeutically effective amount of a GLP-1 molecule, wherein the administration is after the onset of one or more of the following symptoms: chest pain lasting longer than 15 minutes, chest pain at rest, chest pain following minimal exertion, nausea, shortness of breath, palpitations, or dizziness. The above method, wherein the patient has not suffered a Q-wave MI prior to the onset of the symptom or symptoms. The above method, wherein the patient is suffering from unstable angina. The above method, wherein the patient is suffering from non-Q-wave cardiac necrosis. The above method, wherein the patient has a blood troponin I level of no more than 0.4 ng/ml. The above method, wherein the patient has a blood troponin T level of no more than 0.1 ng/ml. The above method, wherein the patient does not have elevated blood creatine kinase myocardial isoenzyme. The above method, wherein the patient does not have ST-segment elevation. The above method, wherein the patient does not exhibit a pathological Q-wave. The above method, wherein the administration occurs between the time of onset of the one or more symptoms, and the time the patient suffers a Q-wave MI. The above method, further comprising the step of continuing the administration of a GLP-1 molecule during the time that the patient suffers a Q-wave MI. The above method, further comprising the step of continuing the administration of a GLP-1 molecule after the time the patient suffers a Q-wave MI. The above method, wherein the patient has ischemic heart disease, or is at risk for developing ischemic heart disease. The above method, wherein the patient has one or more of the following cardiac abnormalities: congestive heart failure, worsening heart murmur due to mitral regurgitation, or evidence of cardiac conduction disturbances. The above method, wherein the patient has a normal ECG. The above method, wherein the patient has stable angina. The above method, wherein the patient administers the GLP-1 to himself. The above method, wherein the GLP-1 is administered in the form of a GLP-1-stick. The above method, wherein the GLP-1 is administered in a single dose. The above method, wherein the GLP-1 is administered in more than one dose. The above method, wherein the GLP-1 is administered continuously. The above method, wherein glucose, or a potassium salt, or a combination thereof, is co-administered with the GLP-1.

(3) A method for treating a patient suffering from stable angina, comprising administration of a GLP-1 molecule. The above method, wherein the administration is continuous.

(4) A method for performing angioplasty on a patient in need thereof, comprising administering a GLP-1 molecule to the patient during the angioplasty procedure. The above method, further comprising administering a GLP-1 molecule to the patient prior to the angioplasty procedure. The above method, further comprising administering a GLP-1 molecule to the patient following the angioplasty procedure.

(5) A method for treatment of a patient with ischemic heart disease, or is at risk for developing ischemic heart disease, and who exhibits one or more of the following symptoms: nausea, shortness of breath, palpitations, or dizziness, and further wherein the patient does not exhibit chest pain, comprising administering to the patient a therapeutically effective amount of a GLP-1 molecule, wherein the patient is not suffering a Q-wave MI. The above method, wherein the patient has a normal ECG.

(6) A method for increasing the time during which thrombolytic therapy will be effective following the first symptom of cardiac distress, comprising administering a therapeutically effective amount of a GLP-1 molecule after the onset of one or more of the following symptoms: chest pain lasting longer than 15 minutes, chest pain at rest, chest pain following minimal exertion, nausea, shortness of breath, palpitations, or dizziness.

(7) A kit comprising one or more doses of a GLP-1 molecule, the kit comprising a device selected from the group consisting of an insulin-type syringe, a "pen" injector that delivers a metered dose, a needle-less injector, a liquid-formulation, a dry-powder inhaler, a buccal tablet, and a sublingual tablet.

DETAILED DESCRIPTION OF THE PREFERRED EMBODIMENTS

Thus, the invention encompasses novel methods for the treatment of acute coronary syndrome, particularly unstable angina and non-Q-wave cardiac necrosis, with a GLP-1 molecule. The methods of the present invention can be used beginning at the earliest stages of ACS, prior to development of a Q-wave MI, to prevent damage associated with ischemia that occurs during Q-wave MI. The inventive therapeutic methods that use a GLP-1 molecule reverse or ameliorate the ischemia-induced damage that occurs during UA and NQCN. The methods of the invention further comprise continuing the treatment with a GLP-1 molecule during or after the time that a patient suffers from a QMI.

Definitions

As used in this application, a "Q-wave MI" denotes a condition that is diagnosed in a patient who exhibits a pathological Q-wave, as indicated by electrocardiogram (ECG), and who has one or more of the following symptoms and signs: (1) ST elevation, as measured by ECG; (2) elevated blood levels of troponin I and troponin T, associated with a Q-wave MI; (3) elevated blood creatine kinase myocardial isoenzyme (CK-MB) level, associated with a Q-wave MI; and (4) elevated blood lactate dehydrogenase level, associated with a Q-wave MI. Typically, the pathological Q-wave will be exhibited within about 6–18 hours of a total coronary occlusion. The skilled artisan will understand that a diagnosis of Q-wave MI generally indicates the presence of a totally occluded coronary artery. Furthermore, the skilled artisan will understand that the diagnosis of QMI is one of medical judgment.

"Elevated" troponin I levels of greater than 0.4 ng/ml typically are highly predictive of some degree of Q-wave MI. Antman et al., *New Engl. J. Med.*, 335; 1342 (1996). "Elevated" troponin T levels of greater than 0.1 ng/ml typically are highly predictive of some degree of Q-wave MI. Ohman et al., *New Engl. J. Med.*, 335; 1333 (1996). Increased troponin levels can be observed within about 2 hours of a QMI. See, e.g., Klootwijk et al., *A.C.S.* 353, 10 (1999); U.S. Pat. No. 5,690,103.

"Elevated" CK-MB levels of greater than 10 U/liter and greater than 5% of total CK enzyme activity typically are highly predictive of some degree of Q-wave MI. Thompson et al., *M.J.A.* 171; 153 (1999). Increased CK-MB levels can be observed within about 3 to 4 hours after QMI. See, e.g., U.S. Pat. No. 5,690,103.

One example of "elevated" LDH levels that are associated with a QMI is a significant rise in LDH and at least one plasma sample showing LDH1 levels greater than LDH2 levels. Furlong et al., *Clin. Chem.* 96; 134 (1991). Another example of such elevated levels is two serum values of LDH that are at least two standard deviations above the normal range. Malmberg et al., *J. Am. Col. Cardiol.* 26; 57 (1995).

Q-wave MI is typically accompanied by chest pain of at least 15 minutes in duration. However, diagnosis of chest pain alone does not indicate that the patient is suffering from Q-wave MI.

The diagnostic criteria for UA and NQCN are quite different from those for Q-wave MI, although all can be characterized by chest pain. As used herein, a patient suffering from "unstable angina" denotes a patient who has one or more of the following symptoms and signs: (1) ST segment depression, as measured by ECG; (2) slightly elevated troponin T levels, of no more than 0.1 ng/ml; or (3) slightly elevated troponin I levels, of no more than 0.4 ng/ml. In contrast to Q-wave MI, CK-MB and LDH levels are typically not elevated during UA. Also in contrast to Q-wave MI, a patient with UA typically has no ST segment elevation nor any pathological Q-wave. Finally, UA can be diagnosed solely on the basis of chest pain, typically chest pain lasting longer than 15 minutes, chest pain at rest, or chest pain following minimal exertion and that is poorly responsive to sublingual nitrates. Alternatively, even in the absence of chest pain, a patient can be diagnosed with UA if previously diagnosed with ischemic heart disease (IHD) or is considered to be at strong risk for developing IHD, and who presents with nausea, shortness of breath, palpitations, or dizziness. Furthermore, the skilled artisan will understand that the diagnosis of UA is one of medical judgment.

As used herein, "ischemic heart disease" denotes disease of cardiac tissue that results from a decreased oxygen supply to the cardiac tissue that is due to reduced coronary artery blood flow. Typically, this reduced blood flow results from the partial or complete obstruction of blood vessels that service the heart. A diagnosis of IHD can be based on the presence of chronic, stable angina, elicited by exercise (also known as "exertional angina") that is relieved by sublingual nitrates. A diagnosis of IHD also can be based on an ECG reading that is consistent with IHD, such as one exhibiting ST segment deviations and/or T wave inversions.

NQCN can present similarly to UA. As used herein, a patient suffering from "non-Q wave cardiac necrosis" denotes a patient who does not have a pathological Q-wave, but who has one or more of the following symptoms and signs: (1) ST segment elevation or depression, as measured by ECG, (2) elevation of troponin I, greater than 0.4 ng/ml; (3) elevation of troponin T, greater than 0.1 ng/ml; or (4) elevation of CK-MB greater than 10 U/liter within 24–48 hours of onset of symptoms. Typically, a NQCN patient will present with chest pain of cardiac origin lasting longer than 15 minutes, with or without ST segment elevation or depression. Furthermore, the skilled artisan will understand that the diagnosis of NQCN is one of medical judgment.

"Angina" or "angina pectoris" generally refers to chest pain resulting from an insufficient blood supply to the heart. Angina pectoris is a recurring symptom and usually occurs in the form of chest discomfort (tightness, fullness, squeezing, heaviness, burning or pain) in the center of the chest and/or over the left breast. The discomfort may move to the left shoulder and arm, although it may move to both shoulders/arms, throat, jaw, or even the lower portion of the chest or upper abdomen. It may be accompanied by shortness of breath, sweating, weakness, dizziness, nausea, or numbness in the shoulders, arms, or hands. Symptoms of angina pectoris are typically triggered by physical exertion. The symptoms are generally brief, last only 2–3 minutes and subside promptly with cessation of exercise or following the use of a nitroglycerin tablet, which typically is administered via a sublingual route. This pattern of pain is known as "stable angina." "Chronic stable angina" generally is used to describe a patient who routinely exhibits the symptoms of "stable angina" over a prolonged period of weeks, months, or years.

As used herein "symptom of cardiac distress" is used to denote one or more of the following: chest pain lasting longer than 15 minutes, chest pain at rest, chest pain following minimal exertion, nausea, shortness of breath, palpitations, or dizziness. The skilled artisan will recognize that palpitations generally are recognized by a "racing" heartbeat, beating more quickly than normal, during rest conditions.

As used herein, a "GLP-1 molecule" includes the following. Mammalian GLP peptides and glucagon are encoded by the same gene. In the ileum the precursor is processed into two major classes of GLP peptide hormones, namely GLP-1 and GLP-2. GLP-1(1–37) has the sequence: His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:1). GLP-1 (1–37) is amidated by post-translational processing to yield GLP-1 (1–36)$NH_2$, which has the sequence: His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:2), or is enzymatically processed to yield GLP-1(7–37), which has the sequence: His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:3). GLP-1(7–37) can also be amidated to yield GLP-1(7–36)amide, which is the natural form of the GLP-1 molecule, and which has the sequence: His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:4). Likewise, GLP-1(1–36) amide can be processed to GLP-1(7–36)amide.

Intestinal L cells secrete GLP-1(7–37) (SEQ ID NO:3) and GLP-1(7–36)$NH_2$ (SEQ ID NO: 4) in a ratio of 1 to 5. These truncated forms of GLP-1 have short half-lives in vivo (less than 10 minutes), and are inactivated by an aminodipeptidase IV to yield: Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5), and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:6), respectively. It has been speculated that the peptides Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:6) affect hepatic glucose production, but do not stimulate production or release of insulin from the pancreas.

As used in this specification, the term "GLP-1 molecule" includes GLP-1(1–37), GLP-1(1–36)$NH_2$, GLP-1(7–37) GLP-1(7–36)$NH_2$ ("GLP-1) (7–36)amide") (collectively referred to as "GLP-1 peptides"). The present invention includes the use of recombinant human GLP-1 peptides and GLP-1 peptides derived from other species, whether recombinant or synthetic.

"GLP-1 molecule" further denotes biologically active variants, analogs, and derivatives of GLP-1 peptides. "Biologically active," in this context, means having GLP-1 (7–36) biological activity, but it is understood that the variant, analog, or derivative can be either less or more potent than native GLP-1(7–36)amide, a native, biologically active form of GLP-1. See Goke & Byrne,*Diabetic Medicine.* 13; 854 (1996). GLP-1 molecules of the present invention include polynucleotides that express agonists of GLP-1 (i.e., activators of the GLP-1 receptor molecule and its secondary messenger activity found on, inter alia, insulin-producing β-cells). GLP-1 mimetics that also are agonists of β-cells include, for example, chemical compounds specifically designed to activate the GLP-1 receptor. Included as GLP-1 molecules are any molecules, whether they be peptides, peptide mimetics, or other molecules that bird to or activate a GLP-1 receptor, such as the GLP-1(7–36)amide receptor, and its second messenger cascade. GLP-1 molecules include species having insulinotropic activity and that are agonists of (i.e., activate), the GLP-1 receptor molecule and its second messenger activity on, inter alia, insulin producing β-cells.

"GLP-1 molecules" also include peptides that are encoded by polynucleotides that express biologically active GLP-1 variants, as defined herein. Also included in the present invention are GLP-1 molecules that are peptides containing one or more amino acid substitutions, additions or deletions, compared with GLP-1(7–36)amide. In one embodiment, the number of substitutions, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. A "conservative" substitution denotes the replacement of an amino acid residue by another, biologically active similar residue. Examples of conservative substitution include the substitution of one hydrophobic residue, such as isoleucine, valine, leucine, or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

| ORIGINAL RESIDUE | EXEMPLARY SUBSTITUTIONS |
|---|---|
| ALA | SER, THR |
| ARG | LYS |
| ASN | HIS, SER |
| ASP | GLU, ASN |
| CYS | SER |
| GLN | ASN, HIS |
| GLU | ASP, GLU |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that GLP-1 peptide variants include the above described peptides which have been chemically derivatized or altered, for example, peptides with non-natural amino acid residues (e.g., taurine residue, β- and γ-amino acid residues and D-amino acid residues), C-terminal functional group modifications such as amides, esters, and C-terminal ketone modifications and N-terminal functional group modifications such as acylated amines, Schiff bases, or cyclization, such as found, for example, in the amino acid pyroglutamic acid.

Also included in the present invention are peptide sequences having greater than 50% sequence identity, and preferably greater than 90% sequence identity to (1) SEQ ID NOS: 1, 2, 3, 4; and (2) to truncated sequences thereof. As used herein, sequence identity refers to a comparison made between two molecules using standard algorithms well known in the art. The preferred algorithm for calculating sequence identity for the present invention is the Smith-Waterman algorithm, where SEQ ID NO:1 is used as the reference sequence to define the percentage identity of homologs over its length. The choice of parameter values for matches, mismatches, and inserts or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and $-\frac{1}{3}$ for a mismatched residue (a residue being either a single nucleotide or single amino acid). Waterman, *Bull. Math. Biol.* 46; 473 (1984). Insertions and deletions (indels), x, are weighted as $X_k=1+k/3$, where k is the number of residues in a given insert or deletion. Id.

For instance, a sequence that is identical to the 42-amino acid residue sequence of SEQ ID NO: 1, except for 18 amino acid substitutions and an insertion of 3 amino acids, would have a percent identity given by:

$$[(1\times42 \text{ matches})-(\tfrac{1}{3}\times18 \text{ mismatches})-(1+\tfrac{3}{3} \text{ indels})]/42=81\% \text{ identity.}$$

Also included in "GLP-1 molecules" of the present invention are six peptides in Gila monster venoms that are homologous to GLP-1. Their sequences are compared to the sequence of GLP-1 in Table 1.

TABLE 1

Position 1 a. H A E G T F T S D V S S Y L E G Q A A K E F I A W L V K G R (NH₂)

b. H S D G T F T S D L S K Q M E E E A V R L F I E W L K N G G P S S G A P P P S (NH₂)

c. D L S K Q M E E E A V R L F I E W L K N G G P S S G A P P P S (NH₂)

d. H G E G T F T S D L S K Q M E E E A V R L F I E W L K N G G P S S G A P P P S (NH₂)

e. H S D A T F T A E Y S K L L A K L A L Q K Y L E S I L G S S T S P R P P S S f. H S D A T F T A E Y S K L L A K L A L Q K Y L E S I L G S S T S P R P P S g. H S D A I F T E E Y S K L L A K L A L Q K Y L A S I L G S R T S P P P (NH₂)

TABLE 1-continued

Position 1 h. H S D A I F T Q Q Y S K L L A K L A L Q K Y L A S I L G S R T S P P P (NH$_2$)

```
a = GLP-1(7-36)amide (SEQ. ID NO: 4)
b = exendin 3 (SEQ. ID NO: 7).
c = exendin 4 (9-39(NH₂) (SEQ. ID NO: 8).
d = exendin 4 (SEQ. ID NO: 9).
e = helospectin I (SEQ. ID NO: 10).
f = helospectin II (SEQ. ID NO: 11).
g = helodermin (SEQ. ID NO: 12).
h = Q⁸, Q⁹ helodermin (SEQ. ID No:13).
```

Peptides (a, b, d, e, f, and g) are homologous at positions 1, 7, 11 and 18. GLP-1 and exendins are further homologous at positions, 4, 5, 6, 8, 9, 15, 22, 23, 25, 26 and 29. In position 2, A, S, and G are structurally similar. In position 3, residues D and E (Asp and Glu) are structurally similar. In positions 22 and 23, F (Phe) and I (Ile) are structurally similar to Y (Tyr) and L (Leu), respectively. Likewise, in position 26, L and I are structurally equivalent.

Thus, of the 30 residues of GLP-1, exendins 3 and 4 are identical in 15 positions and equivalent in 5 additional positions. The only positions where major structural changes are evident are at residues 16, 17, 19, 21, 24, 27, 28 and 30. Exendins also have 9 extra residues at the C-terminus.

Agonists of glucagon-like peptide that exhibit activity through the GLP-1(7–36)amide receptor have been described. See EP 0708179 A2; Hjorth et al., *J. Biol. Chem.* 269; 30121 (1994); Siegel et al., Amer. Diabetes Assoc. 57$^{th}$ Scientific Session, Boston (1997); Hareter et al., Amer. Diabetes Assoc. 57$^{th}$ Scientific Session, Boston (1997); Adelhorst et al., *J. Biol. Chem.* 269, 6275 (1994); Deacon et al., 16$^{th}$ International Diabetes Federation Congress Abstracts, *Diabetologia Supplement* (1997); Irwin et al., *Proc. Natl. Acad. Sci. USA* 94; 7915 (1997); Mojsov, *Int. J. Peptide Protein Res.* 40; 333 (1992). Göke & Byrne, *Diabetic Medicine* 13; 854 (1996). Recent publications disclose Black Widow GLP-1 and Ser$^2$ GLP-1. See Holz & Hakner, *Comp. Biochem. Physiol.*, Part B 121; 177 (1998) and Ritzel et al., *J. Endocrinol* 159; 93 (1998).

GLP-1 receptors are cell-surface proteins found, for example, on insulin-producing pancreatic β-cells; the GLP-1(7–36) receptor has been characterised in the art. Methods of determining whether a chemical or peptide binds to or activates a GLP-1 receptor are known to the skilled artisan and are preferably carried out with the aid of combinatorial chemical libraries and high throughput screening techniques.

GLP-1 molecule biological activity can be determined by in vitro and in vivo animal models and human studies as is well known to the skilled artisan. GLP-1 biological activity can be determined by standard methods, in general, by receptor-binding activity screening procedures, which involve providing appropriate cells that express the GLP-1 receptor on their surface, for example, insulinoma cell lines such as RINmSF cells or INS-1 cells. See Mojsov, *Int. J. Peptide Protein Res.* 40; 333 (1992) and EP 0708179 A2. Cells that are engineered to express a GLP-1 receptor also can be used. In addition to measuring specific binding of tracer to membrane using radioimmunoassay methods, cAMP activity or glucose dependent insulin production can also be measured. In one method, a polynucleotide encoding the GLP-1 receptor is employed to transfect cells so that they express the GLP-1 receptor protein. Thus, for example, these methods may be employed for screening for a receptor agonist by contacting such cells with compounds to be screened and determining whether such compounds generate a signal (i.e., activate the receptor). Other screening techniques include the use of cells that express the GLP-1 receptor, for example, transfected CHO cells, in a system to measure extracellular pH or ionic changes caused by receptor activation. For example, potential agonists may be contacted with a cell that expresses the GLP-1 protein receptor and a second messenger response (e.g., signal transduction or ionic or pH changes), may be measured to determine whether the potential agonist is effective.

Polyclonal and monoclonal antibodies can be utilized to detect purify and identify GLP-1-like peptides for use in the methods described herein. Antibodies such as ABGA1178 detect intact GLP-1(1–37) or N-terminally-truncated GLP-1(7–37) or GLP-1(7–36)amide. Other antibodies detect the end of the C-terminus of the precursor molecule, a procedure that allows one—by subtraction—to calculate the amount of biologically active, truncated peptide (i.e., GLP-1(7–37) amide). Orskov et al., *Diabetes* 42; 658 (1993); Orskov et al., *J. Clin. Invest.* 1991, 87; 415 (1991).

The GLP-1 molecules of the invention that are peptides that can be made by solid-state chemical peptide synthesis. Such peptides can also be made by conventional recombinant techniques using standard procedures described in, for example, Sambrook & Maniaitis. "Recombinant," as used herein, means that a gene is derived from a recombinant (e.g., microbial or mammalian) expression system that has been genetically modified to contain a polynucleotide encoding a GLP-1 molecule as described herein.

The GLP-1 molecule peptides of the present invention may be a naturally purified product, or a product of synthetic chemical procedures, or produced by recombinant techniques from prokaryotic or eukaryotic hosts (for example, by bacteria, yeast, higher plant, insect, or mammalian cells in culture or in vivo). Depending on the host employed in a recombinant production procedure, the polypeptides of the present invention are generally non-glycosylated, but may be glycosylated.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography (HPLC) can be employed for final purification steps.

Particularly preferred GLP-1 molecules of the invention are GLP-1(7–36)amide, GLP-1(7–37), and exendin-4.

Formulation and Administration of GLP-1 for Therapeutic Treatment

Typically, a GLP-1 molecule of the invention will be administered in a parenteral formulation. In one preferred embodiment, the GLP-1 is in a liquid formulation. In a particularly preferred embodiment, the GLP-1 molecule will be administered, at the first onset of symptoms, using a syringe comprising a liquid formulation of a pharmaceutically acceptable form of a GLP-1 molecule. Such a syringe, or "GLP-stick" can be used for self-administration of a GLP-1 molecule. Syringes for self-administration of drugs are well known in the art. See, e.g., U.S. Pat. Nos. 5,980,491 and 5,984,900. Also well known in the art are tuberculin-type syringes that are used for insulin injections.

Other well known methods for administration of a GLP-1 molecule to a patient suffering from UA or NQCN also can be employed in the methods of the invention. These administration methods include, but are not limited to, subcutaneous or micropressure injection, external or implant pump, depot injection, and other types of prolonged application dispensing devices. Other methods of administration, such as transdermal or transmembrane administration, using patch or buccal means, also can be employed. Oral administration also may be suitable. Pulmonary administration, such as inhalation, can also be employed.

Accordingly, embodiments of the invention include a GLP-1 molecule contained in any type of syringe or device that is suitable for parenteral administration, also known as "kits." These include, but are not limited to, a pen-type syringe, an insulin-type syringe, a "pen" injector that delivers a metered dose, a needle-less injector, an external or implant pump, and a dry powder inhaler. Such kits comprise one or more doses of a GLP-1 molecule. Also included in the invention are buccal or sublingual tablets comprising a GLP-1 molecule.

The amount of a GLP-1 molecule that should be administered will vary according to the severity of the conditions and the patient. For self-administration using a GLP-stick, the total dose typically will be 0.1–10.0 nmol/kg, preferably 1.5 nmol/kg. An advantage of using GLP-1(7–36)amide is that high doses can be used without consequent hypoglycemia, because the action of GLP-1(7–36)amide is dependent on glucose levels. Therefore, doses of up to 10.0 nmol/kg can be used without adverse effects. For continuous administration, levels of 0.1 to 10.0 pmol/kg/min, preferably 1 to 4 pmol/kg/min, are used. For continuous subcutaneous administration, levels of about 0.5 to 50 pmol/kg/min or 0.5 to 50 pmol/kg/min, preferably about 1 to 10 pmol/kg/min or 1 to 10 pmol/kg/min, are used.

The timing and dosage of a GLP-1 molecule, according to the methods of the invention, will depend on the nature of the condition being treated. As discussed here, a GLP-1 molecule may be administered as soon as there is a symptom of cardiac distress, and the administration can be continued, either continuously or or an intermittent basis, for as long as necessary. For example, the patient can self-administer a GLP-1 molecule at the first symptom of cardiac distress, and a GLP-1 molecule can thereafter be administered during the time that the patient is in transit to the hospital, and continued during hospitalization, as necessary. Thus, the GLP-1 molecule can be administered at the first cardiac symptom, up until the time a Q-wave MI occurs. In the event that such a QMI occurs following the administration of a GLP-1 molecule, the pretreatment of the patient with GLP-1 will ameliorate the tissue damage that results from the MI. In alternative embodiments, the invention includes methods of administering GLP-1 at the first symptom of cardiac distress, and continuing that administration during the time that the individual suffers a QMI. In still further embodiments, the invention includes continuing administration of a GLP-1 molecule after the individual has suffered a QMI. The administration of GLP-1 following a QMI will ameliorate the tissue damage that results from the QMI and subsequent reperfusion-induced injury.

Pharmaceutically acceptable salts of a GLP-1 molecule also can be used in the methods of the invention. Both organic and inorganic acid addition salts can be employed, using acids that include, but are not limited to, proprionic, succinic, lactic, malic, citric, acetic, benzoic, oxalic, carbonic, hydrochloric, hydrobromic, hydroiodic, sulfuric, and phosphoric.

A GLP-1 molecule, or a pharmaceutically acceptable salt thereof, can be formulated with a "pharmaceutically acceptable carrier or excipient," which includes, for example, saline, buffered saline, dextrose, water, glycerol, ethanol, lactose, phosphate, mannitol, arginine, trehalose, and combinations thereof, and further includes agents that enhance the half-life in vivo of GLP-1, or a biologically active variant, analog, or derivative thereof, in order to enhance or prolong the biological activity of the peptide or variant, analog, or derivative thereof.

Therapeutic Methods Using GLP-1

GLP-1 molecules, particularly GLP-1(7–36)amide, act to quickly suppress FFA levels and to optimize aberrant glucose metabolism in the heart, via a variety of mechanisms. In particular, GLP-1(7–36)amide acts to suppress glucagon secretion from pancreatic $\alpha$-cells. GLP-1(7–36)amide has no known serious adverse side effects and can be administered at high doses without risking hypoglycemia or hyperglycemia. GLP-1 molecules are ideal for optimizing glucose metabolism in a variety of individuals, including those with impaired glucose tolerance, and those with elevated or aberrant blood glucose levels that are induced by certain conditions, such as stress-related cardiac conditions, and cardiac ischemia induced by UA or NQCN. The present invention contemplates treatment of individuals suffering from one or more of a variety of cardiac system disturbances or disorders, including but not limited to UA and NQCN, which are described in this application. In other embodiments, the inventive early stage treatment of UA can optionally be continued during and after a QMI. In various embodiments of the invention, these therapeutic methods include treatment of individuals with diabetes, including NIDDM, impaired glucose tolerance, and stress hyperglycemia.

In other preferred embodiments, the therapeutic methods of the invention do not include the treatment of an individual with type 2 diabetes (also known as "Non-Insulin Dependent Diabetes Mellitus" or "NIDDM"). In still other preferred embodiments, the therapeutic methods of the invention do not include treatment of an individual with any type of diabetes. In additional embodiments, the therapeutic methods of the invention do not include the treatment of an individual with impaired glucose tolerance.

In yet other embodiments of the present invention, the therapeutic methods do not include the treatment of an, individual suffering from a Q-wave MI. In additional embodiments, the therapeutic methods of the present invention do not include the treatment of an individual suffering from a pathological Q-wave. The methods of the invention also do not include the treatment of an individual suffering from a ST elevation, or ST elevation followed by T wave inversion. In other embodiments, the present therapeutic, methods do not include the treatment of an individual having at least two values of serum CK-MB and CK that are at least two standard deviations above the normal range, 10–16 hours after the onset of a symptom such a chest pain. In still other embodiments, the present therapeutic methods do not include treatment of an individual having at least two values of serum lactate dehydrogenase that are at least two standard deviations above the normal range, and an isoenzyme pattern typical of QMI, within 48–72 hours after onset of a symptom such as chest pain.

As discussed above, ischemic cardiac tissue switches to anaerobic glucose metabolism, from aerobic oxidation of FFA. Glucose oxidation consumes less energy than FFA oxidation, and hence glucose oxidation preserves borderline cardiac efficiency and increases cardiac efficiency during ischemia. Kantor et al., *Am. J. Med. Sci.* 318; 3 (1999). However, this switch to glucose metabolism during ischemia is usually incomplete because glycolysis and glucose oxidation are inhibited in the presence of insulin antagonism and high glucagon levels. In particular, excess blood FFA accumulate, and incomplete metabolism of FFA, or FPA oxidation, creates highly toxic free radicals that cause myocardial tissue damage.

Treatment with GLP-1 will ameliorate the adverse effects of cardiac tissue ischemia. First, GLP-1 molecules promote glucose utilization by cardiac tissue, providing valuable energy. GLP-1 thus optimizes tissue utilization and metabolism of glucose, the major energy source during cardiac ischemia. Second, GLP-1-molecule-mediated suppression of glucagon will limit insulin antagonism and reduce circulating FFAs, thus favoring glucose oxidation. These effects of GLP-1 are critical, because glucose oxidation consumes less oxygen than fatty acid oxidation.

Because of these beneficial effects of GLP-1 on glucose metabolism, the therapeutic methods of the present invention will extend the time window during which thrombolytic therapy, such as TPA or angioplasty, will be effective, following the first symptom of cardiac distress, such as chest pain lasting longer than 15 minutes, chest pain at rest, chest pain following minimal exertion, nausea, shortness of breath, palpitations, or dizziness. Thrombolytic therapy is known in the art for treatment of coronary artery occlusion. See, e.g., Zaacks et al., *J.A.C.C.* 33; 107 (1999). It also is known that thrombolytic therapy for QMI is only effective during a relatively brief time period following QMI or strong clinical suspicion of QMI. Id.

TPA therapy generally is indicated when there has been (1) a diagnosed Q-wave MI, or (2) strong clinical suspicion of a Q-wave MI, accompanied by ST segment elevation and an increase in troponins I and troponin T associated with QMI, and/or an increase in CK-MB that is associated with a QMI. Percutaneous transluminal coronary angioplasty (PTCA) is typically performed in a patient with a confirmed or suspected QMI, NQCN, or UA, when there is a strong suspicion of a developing adverse cardiac event. PTCA is often used to treat any individual suffering from ACS. Accordingly, the therapeutic methods of the present invention will extend the time period, following cardiac distress, during which angioplasty and/or TPA therapy will be effective.

It is known in the art that the PTCA procedure itself can result in the release of small emboli, which can, in turn, cause cardiac ischemia when they become lodged in blood vessels. Accordingly, another embodiment of the invention is the treatment of a patient undergoing PTCA, with a GLP-1 molecule. The GLP-1 molecule will optimize metabolism, and hence ameliorate or prevent the ischemic damage caused by the PTCA-induced release of emboli. In one embodiment, the GLP-1 molecule is administered continuously during the PTCA procedure. In other embodiments, administration of a GLP-1 molecule begins before the PTCA procedure, and continues during the procedure. I yet other embodiments, the GLP-1 molecule administration is continued after the PTCA procedure is completed. In yet other embodiments, the invention includes administering a GLP-1 molecule to a patient undergoing PTCA, wherein the patient has not suffered a Q-wave MI. In other embodiments, the patient has not exhibited a pathological Q-wave.

Acute Coronary Syndrome

It is an object of the present invention to provide a method of treating a patient suffering from acute coronary syndrome, comprising treatment of the patient with a therapeutically effective amount of a GLP-1 molecule, such as GLP-1(7–36) amide. In particular, the present invention provides methods of treating patients suffering from unstable angina and/or a non-Q wave cardiac necrosis. In preferred embodiments, a patient suffering from unstable angina treated using the inventive method has one or more of the following conditions: (1) a blood troponin I level of no more than 0.4 ng/ml; (2) a blood troponin T level of no more than 0.1 ng/ml; (3) does not have elevated CK-MB associated with QMI; (4) does not have elevated blood lactate dehydrogenase associated with QMI; (5) does not have ST-segment elevation; or (6) does not exhibit a pathological Q-wave.

In a preferred embodiment, the patient has the following symptoms: (1) a blood troponin I level of no more than 0.4 ng/ml; (2) a blood troponin T level of no more than 0.1 ng/ml; (3) does not have elevated blood creatine kinase associated with QMI; (4) does not have elevated blood lactate dehydrogenase associated with QMI; (5) does not have ST-segment elevation; and (6) does not exhibit a pathological Q-wave.

It also is an object of the invention to provide a method for treating a patient suffering from non-Q-wave cardiac necrosis, wherein the patient does not have elevated blood CK-MB associated with QMI. In another embodiment, the patient has a blood troponin I level of no more than 0.4 ng/ml. In another embodiment, the patient has a blood troponin T level of no more than 0.1 ng/ml. In another embodiment, the patient does not have ST-segment elevation. In another embodiment, the NQCN patient does not have elevated blood lactate dehydrogenase associated with QMI. In still other embodiments, the patient does not have elevated blood lactate dehydrogenase or elevated creatine kinase. In still another embodiment, the patient does not exhibit a pathological Q-wave.

The use of a GLP-1 molecule in the early stages of ACS, during UA and/or NQCN, will serve to optimize myocardial use of energy substrates, and will limit ischemia-induced damage. Such use of GLP-1 will have the effect of decreasing tissue damage, morbidity and mortality that is associated with UA, NQCN, and Q-wave MI.

The invention also encompasses a method for treatment of an individual with an established diagnosis of ACS (UA or NQCN) in whom there is—as yet—no evidence of an established Q-wave MI, in order to preserve and salvage at-risk myocardial tissue in the ischemic and peri-ischemic zones. Such treatment will comprise the administration of intravenous GLP-1 by continuous infusion, in an appropriate liquid formulation, at a dose of 0.1–10.0 pmol/kg/min, preferably 1.0–3.0 pmol/kg/min, for periods of several hours and up to 10 days, preferably for one to three days. Said continuous intravenous infusion of GLP-1 can be an isolated treatment, or in conjunction with the co-administration of intravenous glucose, as a continuous infusion of a 5–10% solution, and/or the co-administration of potassium, as a continuous infusion of a solution of a suitable potassium salt (such as potassium chloride or potassium acetate) that will supply sufficient potassium to maintain "normal" plasma potassium levels of about 4–5 mM. Typically the solution for administration of potassium will be about 40 mM, but the skilled artisan will recognize that any concentration of potassium can be used, so long as it supplies the desired dosage to the patient. Suitable rates for administration of potassium are between about 40 and about 120 μmol/kg/hr. Co-infusion with glucose is known to enhance and maintain the insulinotropic drive of GLP-1; co-infusion of potassium is known to correct the hypokalemia that can potentially result from intracellular potassium shifts that accompany insulin-mediated glucose uptake.

Patients Diagnosed With, or at Risk of Developing, IHD

It is known that individuals with diagnosed IHD, as evidenced inter alia by previously documented ST segment changes or by clinical features described elsewhere in this application, or those with a family history of severe IHD, are at high risk for suffering from UA, NQCN, and Q-wave MI. Zaacks et al., *J. Am. Col. Cardiol.* 33; 107 (1999). According to one aspect of the invention, a patient who has been previously diagnosed with IHD, or is at strong risk for IHD, can then self administer GLP-1 when he/she experiences a symptom that could be indicative of UA, NQCN, or future Q-wave MI. In other words, if such a patient experiences chest pain lasting longer than 15 minutes, chest pain at rest, or chest pain following minimal exertion, nausea, shortness of breath, palpitations, or dizziness, he/she can immediately administer a dose of GLP-1, using a GLP-stick. This may serve to prevent or ameliorate the damage that would be caused by a future cardiac event. Thus, the invention includes a method for treatment of a patient that has not suffered a Q-wave MI, but has been diagnosed with IHD or is at strong risk for IHD, comprising administering to said individual GLP-1, after onset of one or more of the of the following symptoms: chest pain lasting longer than 15 minutes, chest pain at rest, chest pain following minimal exertion, nausea, shortness of breath, palpitations, or dizziness.

The invention also encompasses a method for treatment of an individual who previously has been diagnosed with likely IHD but with a normal ECG. Myerburg et al., "Electrocardiography", In HARRISON'S PRINCIPALS OF INTERNAL MEDICINE (Isserbacher et al., eds.), 9th ed., pages 999–1011 (McGraw Hill, Tokyo, 1980). The diagnosis of IHD is based on presence of chronic, stable angina, elicited by exercise (also known as "exertional angina") and relieved by sublingual nitrates. Such an individual ray present with symptoms consistent with a diagnosis of UA but have no ECG changes. These symptoms include: chest pain (angina) of increased frequency, severity, or duration, provoked by mild exercise or at rest, where these symptoms are clearly different and more severe than the previously diagnosed chronic, stable angina, or where these symptoms appear in the context of recently diagnosed IHD. This typically occurs about 2 weeks to about 2 months before the onset of UA. When a symptom of cardiac distress appears, as described elsewhere in this application, GLP-1 should be self-administered at the earliest sign of such a symptom.

The invention additionally includes a method for treatment of a patient with stable angina, comprising continuous administration of a GLP-1 molecule. Such administration may be in the form of a patch suitable for transdermal administration. Other suitable methods of administration include continuous subcutaneous infusion, repeated subcutaneous injection, and buccal, oral, or inhaled administration. Still further embodiments include administration using any other method of administration described in this application. The GLP-1 molecule will serve to benefit the coronary tissue through optimizing metabolism.

The invention also encompasses a method for treatment of an individual who previously has been diagnosed as being at strong risk for IHD, because of a family history of severe IHD or a family history of IHD and associated co-morbidities. "Family history of severe IHD" and "family history of IHD and associated co-morbidities" are collectively referred to herein as "family history of IHD." As used in this application, a "family history of severe IHD" denotes a history of a first-degree relative who suffered one or more episodes of acute MI at age 50 or younger, or died as a result of an acute MI or from post-MI heart failure at age 60 or younger; "family history of IHD and associated co-morbidities" denotes a history of angina or MI in a first-degree relative plus the presence in the proband of one or more of the following co-morbid conditions: diabetes, hypertension, hypercholesterolemia or hyperlipidemia, obesity, or history of smoking. When a symptom of cardiac distress appears, as defined above, GLP-1 should be self-administered at the earliest sign.

The invention also encompasses a method for treatment of an individual who exhibits one or more symptoms (chest pain lasting longer than 15 minutes, chest pain at rest, chest pain following minimal exertion, nausea, shortness of breath, palpitations, or dizziness), but who previously had no specific signs and symptoms of IHD—i.e., no previous episodes of chest pain of cardiac origin (angina) and no previously documented changes on ECG consistent with IHD (such as ST segment deviations and/or T wave inversions)—and who has no specific family history of IHD, but who likely has underlying, undiagnosed IHD because of cardiac abnormalities not ascribed to other specific etiologies. These cardiac abnormalities include: (1) congestive heart failure, as evidenced, for example, by shortness of breath on mild exertion or at rest, exercise limitations, signs of pulmonary edema, and peripheral edema; (2) worsening heart murmur due to mitral regurgitation; or (3) evidence of cardiac conduction disturbances, such as left bundle branch block on ECG, atrial or ventricular extrasystoles, atrial fibrillation, or other arrhythmias.

Therefore, the invention includes a method for the treatment of a patient, comprising administering to the patient a therapeutically effective amount of a GLP-1 molecule, wherein said administration occurs after the onset of one or more of the following symptoms: (1) chest pain lasting longer than 15 minutes, (2) chest pain at rest, (3) chest pain following minimal exertion, (4) nausea, (5) shortness of breath, (6) palpitations, or (7) dizziness, wherein said patient has one or more of the following cardiac abnormalities: (1) congestive heart failure, as evidenced, for example, by shortness of breath on mild exertion or at rest, exercise limitations, signs of pulmonary edema, and peripheral edema; (2) worsening heart murmur due to mitral regurgitation; or (3) evidence of cardiac conduction disturbances, such as left bundle branch block on ECG, atrial or ventricular extrasystoles, atrial fibrillation, or other arrhythmias.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

EXAMPLES

Animal models may be used to test the efficacy of the administration of GLP-1 to an individual with unstable angina, but without yet having suffered an actual infarction. Rat models and dog models have been found to be particularly well suited for this purpose. In rats, GLP-1 administered during the last 10 min. of a 25 min. ischemia period and then throughout a 2-hour reperfusion period significantly reduced infarct size (30%), and the rats also had significantly improved hemodynamics. In dogs, administration of GLP-1 significantly reduced the stunning period, during reperfusion after a period of subcritical ischemia.

Example 1

Wistar rats were anesthetized with thiopentone sodium. The left anterior descending (LAD) coronary artery was occluded. After 25 minutes of occlusion, reperfusion was allowed for 2 hours. This animal model has been described previously. Zacharowski, et al., *Br. J. Pharmacol.* 128; 945–952 (1999).

GLP-1 (1.5 μg/kg/min) was infused into anesthetized rats (n=10), commencing 10 minutes prior to reperfusion and continuing throughout the 2-hour reperfusion. Controls were sham operated with no occlusion (n=7), LAD occlusion+reperfusion+administration of saline (n=12), and LAD occlusion and reperfusion with a buffer of 10 mM sodium acetate, 5.05% D-mannitol, pH 4.5, ("vehicle") at 1.5 mL/kg/hour (n=10).

Following reperfusion, the coronary artery was reoccluded, and Evans Blue dye (4 ml, 2% w/v) was injected into the left ventricle of the heart via a right carotid artery cannula. Evans Blue stains perfused myocardium, while occluded vascular bed remains uncolored. Animals were then killed by anesthetic overdose and the hearts were removed for examination. Hearts were sectioned and the right ventricular wall was removed. The area at risk (pink) was separated from the non-ischemic tissue (blue). The area at risk (pink) was then cut into smaller pieces and stained with p-nitroblue tetrazolium (NBT; 0.5 mg/ml) for 20 min. at 37° C. In the presence of intact dehydrogenase enzyme systems (viable myocardium), NBT forms a dark blue compound. Areas of necrosis lack the enzyme and remain unstained. Tissue was separated according to staining and weighed to determine infarct size as a percentage of the area at risk.

In rats receiving the saline infusion, the infarct size was 50±3% of the area at risk. In rats receiving the vehicle infusion, the infarct size was 46±4% of the area at risk. In rats receiving the GLP-1 infusion, the infarct size was 31±4% of the area at risk.

When compared with the vehicle group, infusion of GLP-1 caused a statistically significant (p<0.05) reduction in infarct size of approximately 33%. Thus, the systemic administration of (GLP-1 can reduce myocardial infarct size even when administered after occlusion of a coronary artery and prior to onset of reperfusion.

Example 2

Two dogs were studied at baseline before, during, and for 6 hours after a 10-minute complete left circumflex coronary (LCx) occlusion. Each dog underwent occlusion/reperfusion in the presence and absence of GLP-1 infusion for 24 hours, beginning 1 minute prior to reperfusion. GLP-1 infusion enhanced the recovery of ventricular wall regional dysfunction following 10 minutes of coronary artery occlusion. The study shows that the recovery after ischemia and the reduced stunning in the presence of GLP-1 are not due to increased coronary flow compared to controls, but presumably reflect favorable changes in myocardial energetics.

What is claimed is:

1. A method of treating a patient suffering from acute coronary syndrome, comprising administering to the patient a therapeutically effective amount of a GLP-1 molecule, wherein said patient is not suffering from a myocardial infarction.

2. The method of claim 1, wherein the patient is suffering from unstable angina.

3. The method of claim 1, wherein the patient is suffering from non-Q-wave cardiac necrosis.

4. The method of claim 1, wherein the patient has a blood troponin I level of no more than 0.4 ng/ml.

5. The method of claim 1, wherein the patient has a blood troponin T level of no more than 0.1 ng/ml.

6. The method of claim 1, wherein the patient does not have elevated blood creatine kinase.

7. The method of claim 1, wherein the patient does not have ST-segment elevation.

8. The method of claim 1, wherein the patient does not exhibit a pathological Q-wave.

9. A method according to claim 1, wherein said patient exhibits one or more of the following symptoms: chest pain greater than 15 minutes in duration, chest pain at rest, chest pain following minimal exertion that is poorly responsive to sublingual nitrates.

10. A method according to claim 1, wherein said patient has stable angina.

11. A method according to claim 1, wherein said patient administers the GLP-1 to himself.

12. A method according to claim 1, wherein said GLP-1 is administered in the form of a GLP-1-stick.

13. A method according to claim 1, wherein said GLP-1 is administered in a single dose.

14. A method according to claim 1, wherein said GLP-1 is administered in more than one dose.

15. A method according to claim 1, wherein said GLP-1 is administered continuously.

16. A method according to claim 1, wherein glucose, or a potassium salt, or a combination thereof, is co-administered with the GLP-1.

17. A method for treatment of a patient suffering from one or more conditions selected from the group consisting of unstable angina, non-Q-wave cardiac necrosis, ischemic heart disease, and stable angina, comprising administering to said individual a therapeutically effective amount of a GLP-1 molecule, wherein said administration is after the onset of one or more of the following symptoms: chest pain lasting longer than 15 minutes, chest pain at rest, chest pain following minimal exertion, nausea, shortness of breath, palpitations, or dizziness.

18. A method according to claim 17, wherein the patient has not suffered from a Q-wave MI prior to the onset of said symptom or symptoms.

19. The method of claim 17, wherein the patient is suffering from unstable angina.

20. The method of claim 17, wherein the patient is suffering from non-Q-wave cardiac necrosis.

21. The method of claim 17, wherein the patient has a blood troponin I level of no more than 0.4 ng/ml.

22. The method of claim 17, wherein the patient has a blood troponin T level of no more than 0.1 ng/ml.

23. The method of claim 17, wherein the patient does not have elevated blood creatine kinase myocardial isoenzyme.

24. The method of claim 17, wherein the patient does not have ST-segment elevation.

25. The method of claim 17, wherein the patient does not exhibit a pathological Q-wave.

26. A method according to claim 17, wherein said administration occurs between the time of onset of said symptom and the time that the patient suffers a myocardial infarction.

27. A method according to claim 17, wherein said patient has ischemic heart disease.

28. The method of claim 17, wherein said patient also has one or more of the following cardiac abnormalities: congestive heart failure, worsening heart murmur due to mitral regurgitation; or evidence of cardiac conduction disturbances.

29. The method of claim 28, wherein said patient has a normal ECG.

30. A method according to claim 17, wherein said patient has stable angina.

31. A method according to claim 17, wherein said patient administers the GLP-1 to himself.

32. A method according to claim 17, wherein said GLP-1 is administered in the form of a GLP-1-stick.

33. A method according to claim 17, wherein said GLP-1 is administered in a single dose.

34. A method according to claim 17, wherein said GLP-1 is administered in more than one dose.

35. A method according to claim 17, wherein said GLP-1 is administered continuously.

36. A method according to claim 17, wherein glucose, or a potassium salt, or a combination thereof, is co-administered with the GLP-1.

37. A method for treating a patient suffering from stable angina, comprising administration of a GLP-1 molecule.

38. A method according to claim 37, wherein said administration is continuous.

39. A method for treatment of a patient with ischemic heart disease, or at risk for developing ischemic heart disease, and who exhibits one or more of the following symptoms: nausea, shortness of breath, palpitations and dizziness, and further wherein said patient does not exhibit chest pain, comprising administering to the patient a therapeutically effective amount of a GLP-1 molecule, wherein said patient is not suffering from a myocardial infarction.

40. A method according to claim 39, wherein said patient has a normal ECG.

41. A method for increasing the time during which thrombolytic therapy will be effective following the first symptom of cardiac distress, comprising administering a therapeutically effective amount of a GLP-1 molecule after the onset of one or more of the following symptoms:

chest pain lasting longer than 15 minutes, chest pain at rest, chest pain following minimal exertion, nausea, shortness of breath, palpitations, or dizziness, wherein said patient is not suffering from a myocardial infarction.

* * * * *